(12) United States Patent
Harbeson

(10) Patent No.: US 7,687,509 B2
(45) Date of Patent: Mar. 30, 2010

(54) PYRIMIDINECARBOXAMIDE DERIVATIVES

(75) Inventor: Scott L. Harbeson, Cambridge, MA (US)

(73) Assignee: Concert Pharmaceuticals Inc., Lexington, MA (US)

( * ) Notice: Subject to any disclaimer, the term of this patent is extended or adjusted under 35 U.S.C. 154(b) by 23 days.

(21) Appl. No.: 12/169,367

(22) Filed: Jul. 8, 2008

(65) Prior Publication Data

US 2009/0035324 A1 Feb. 5, 2009

Related U.S. Application Data

(60) Provisional application No. 60/948,610, filed on Jul. 9, 2007.

(51) Int. Cl.
*C07D 413/12* (2006.01)
*A61K 31/505* (2006.01)
(52) U.S. Cl. ...................... 514/269; 544/319
(58) Field of Classification Search ................. 544/319; 514/269
See application file for complete search history.

(56) References Cited

U.S. PATENT DOCUMENTS

| 5,304,121 A | 4/1994 | Sahatjian |
| 5,886,026 A | 3/1999 | Hunter et al. |
| 6,099,562 A | 8/2000 | Ding et al. |
| 6,803,031 B2 | 10/2004 | Rabinowitz et al. |
| 7,169,780 B2 | 1/2007 | Crescenzi et al. |

FOREIGN PATENT DOCUMENTS

| WO | WO 2005/087767 | 9/2005 |
| WO | WO 2005/087768 | 9/2005 |
| WO | WO 2006/060711 | 6/2006 |
| WO | WO 2006/060712 | 6/2006 |
| WO | WO 2006/107478 | 10/2006 |

OTHER PUBLICATIONS

Marcus et al., PubMed Abstract (Intervirology 45(4-6):260-6), 2002.*
van Heeswijk et al., PubMed Abstract (Antivir Ther. 6(4):201-29) Dec. 2001.*
Miles, PubMed Abstract (Community Pract. 78(8):292-4) Aug. 2005.*
Demko et al., "Preparation of 5-substituted 1H-tetrazoles from nitriles in water," *J. Org. Chem.*, 2001, 66(24):7945-7950.
Fisher et al., "The Complexities Inherent in Attempts to Decrease Drug Clearance by Blocking Sites of CYP-mediated Metabolism," *Curr. Opin. Drug Discovery Development*, 2006, 9(1):101-109.
Freireich et al., "Quantitative comparison of toxicity of anticancer agents in mouse, rat, hamster, dog, monkey, and man," *Cancer Chemother. Reports*, 1966, 50(4):219-244.
Gannes et al., "Natural abundance variations in stable isotopes and their potential uses in animal physiological ecology," *Comp. Biochem. Physiol.*, 1998, 119A(3):725-737.
Horino et al., "Preparation, structure, and unique thermal [2+2], [4+2], and [3+2] cycloaddition reactions of 4-vinylideneoxazolidin-2-one," *Chem. Eur. J.*, 2003, 9(11):2419-2438.
Houston et al., "Prediction of hepatic clearance from microsomes, hepatocytes, and liver slices," *Drug Metab. Rev.*, 1997, 29(4):891-922.
Houston, "Utility of in vitro drug metabolism data in predicting in vivo metabolic clearance," *Biochem. Pharmacol.*, 1994, 47(9):1469-1479.
Isentress (raltegravir) Tablets, Oct. 2007, Merck & Co., 18-page product brochure.
Iwatsubo et al., "Prediction of In Vivo Drug Metabolism in the Human Liver from In Vitro Metabolism Data," *Pharmacol. Ther.*, 1997, 73(2):147-171.
Kushner et al., "Pharmacological Uses and Perspectives of Heavy Water and Deuterated Compounds," *Can. J. Pharmacol.*, 1999, 77:79-88.
Lavé et al., "The Use of Human Hepatocytes to Select Compounds Based on Their Expected Hepatic Extraction Ratios in Humans," *Pharm. Res.*, 1997, 14(2):152-155.
Obach, "Prediction of Human Clearance of Twenty-nine Drugs from Hepatic Microsomal Intrinsic Clearance Data: An Examination of In Vitro Half-Life Approach and Nonspecific Binding to Microsomes," *Drug Metab. Disp.*, 1999, 27(11):1350-1359.
Sardashti et al., *J. Phys. Chem.*, 1988, 92(16):4620-4632.
Scientific Tables, *Geigy Pharmaceuticals*, Ardsley, N.Y., 1970, p. 537.
Summa et al., "Discovery of Raltegravir, a Potent, Selective Orally Bioavailable HIV-Integrase Inhibitor for the Treatment of HIV-AIDS Infection," *J. Med. Chem.*, 2008, 51:5843-5855.
Tachibana et al., "Sequential O- and N-acylation protocol for high-yield preparation and modification of rotaxanes: synthesis, functionalization, structure, and intercomponent interaction of rotaxanes," *J. Org. Chem.*, 2006, 71(14):5093-5104.
Wada and Hanba, "Natural abundance of carbon, nitrogen, and hydrogen isotope ratios in biogenic substances: Present and future," *Seikagaku*, 1994, 66(1):15-29.
Wade, "Deuterium isotope effects on noncovalent interactions between molecules," *Chemico-Biological Interactions*, 1999, 117:191-217.

* cited by examiner

*Primary Examiner*—Deepak Rao
(74) *Attorney, Agent, or Firm*—Fish & Richardson P.C.

(57) ABSTRACT

This disclosure relates to novel HIV integrase inhibitors their derivatives, pharmaceutically acceptable salts, solvates, and hydrates thereof. This disclosure also provides compositions comprising a compound of this disclosure and the use of such compositions in methods of treating HIV infections.

9 Claims, No Drawings

PYRIMIDINECARBOXAMIDE DERIVATIVES

CROSS-REFERENCE TO RELATED APPLICATIONS

This application claims priority under 35 U.S.C. §119 to U.S. Provisional Application Ser. No. 60/948,610, filed Jul. 9, 2007, incorporated herein by reference in its entirety.

TECHNICAL FIELD

This disclosure relates to novel HIV integrase inhibitors their derivatives, pharmaceutically acceptable salts, solvates, and hydrates thereof. This disclosure also provides compositions comprising a compound of this disclosure and the use of such compositions in methods of treating HIV infections.

BACKGROUND

AIDS or acquired immune deficiency syndrome is a disease of the immune system caused by the HIV virus. In their December 2006 AIDS epidemic update the Joint United Nations Programme on HIV/AIDS and the World Health Organization reported that 39.5 million people worldwide were infected with HIV. Of that number, 4.3 million people were newly infected in 2006.

Raltegravir is a new drug candidate that shows potent in-vitro activity against HIV-1 strains, including those that are resistant to current anti-retroviral drugs. Raltegravir is also known as MK-0518 and by the chemical names, N-[(4-fluorophenyl)methyl]-1,6-dihydro-5-hydroxy-1-methyl-2-[1-methyl-1-[[(5-methyl-1,3,4-oxadiazol-2-yl)carbonyl]amino]ethyl]-6-oxo-4-pyrimidinecarboxamide and N-(2-(4-(4-fluorobenzylcarbamoyl)-5-hydroxy-1-methyl-6-oxo-1,6-dihydropyrimidin-2-yl)propan-2-yl)-5-methyl-1,3,4-oxadiazole-2-carboxamide Raltegravir inhibits the activity of the HIV-1 integrase. It is currently in phase II human clinical trials for the treatment of AIDS (http://www.clinicaltrials.gov/ct/show/NCT00460382; http://www.clinicaltrials.gov/ct/show/NCT00454337).

Despite the beneficial activities of raltegravir, there is a continuing need for new compounds to treat HIV infection.

SUMMARY

Provided herein is a compound of Formula I:

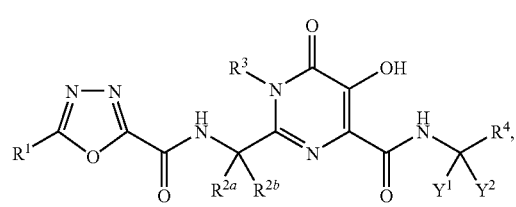

(I)

or a pharmaceutically acceptable salt, solvate, or hydrate thereof, wherein:

each of $R^1$, $R^{2a}$, $R^{2b}$, and $R^3$ is independently selected from $CH_3$, $CDH_2$, $CD_2H$, and $CD_3$;

$Y^1$ and $Y^2$ are each independently selected from H or D;

$R^4$ is selected from:

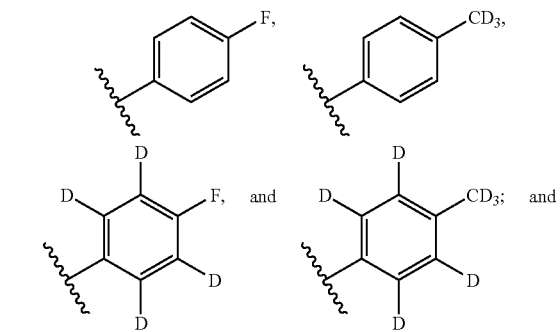

when each R is $CH_3$, at least one Y is D.

In some embodiments, each of $R^1$, $R^{2a}$, $R^{2b}$, and $R^3$ is independently selected from $CH_3$, and $CD_3$.

In some embodiments, $Y^1$ and $Y^2$ are the same.

In some embodiments, $R^{2a}$ and $R^{2b}$ are the same and are selected from $CH_3$ and $CD_3$.

In some embodiments, $R^4$ is selected from

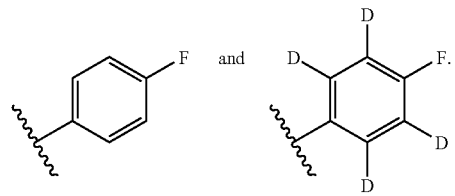

In some embodiments, when $R^4$ is

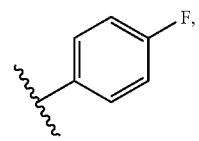

the compound is selected from any one of the compounds set forth in the table below:

| Compound | $R^1$ | $R^{2a}$ | $R^{2b}$ | $R^3$ | $Y^1$ | $Y^2$ |
|---|---|---|---|---|---|---|
| 101 | $CD_3$ | $CH_3$ | $CH_3$ | $CH_3$ | H | H |
| 102 | $CH_3$ | $CD_3$ | $CD_3$ | $CH_3$ | H | H |
| 103 | $CH_3$ | $CH_3$ | $CH_3$ | $CD_3$ | H | H |
| 104 | $CH_3$ | $CH_3$ | $CH_3$ | $CH_3$ | D | D |
| 105 | $CD_3$ | $CD_3$ | $CD_3$ | $CH_3$ | H | H |
| 106 | $CD_3$ | $CH_3$ | $CH_3$ | $CD_3$ | H | H |
| 107 | $CD_3$ | $CH_3$ | $CH_3$ | $CH_3$ | D | D |
| 108 | $CH_3$ | $CD_3$ | $CD_3$ | $CD_3$ | H | H |
| 109 | $CH_3$ | $CD_3$ | $CD_3$ | $CH_3$ | D | D |
| 110 | $CH_3$ | $CH_3$ | $CH_3$ | $CD_3$ | D | D |
| 111 | $CD_3$ | $CD_3$ | $CD_3$ | $CD_3$ | H | H |
| 112 | $CD_3$ | $CH_3$ | $CH_3$ | $CD_3$ | D | D |
| 113 | $CH_3$ | $CD_3$ | $CD_3$ | $CD_3$ | D | D |
| 114 | $CD_3$ | $CD_3$ | $CD_3$ | $CD_3$ | D | D |

In some embodiments, when $R^4$ is

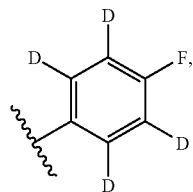

the compound is selected from any one of the compounds set forth in the table below:

| Compound | $R^1$ | $R^{2a}$ | $R^{2b}$ | $R^3$ | $Y^1$ | $Y^2$ |
|---|---|---|---|---|---|---|
| 115 | $CD_3$ | $CH_3$ | $CH_3$ | $CH_3$ | H | H |
| 116 | $CH_3$ | $CD_3$ | $CD_3$ | $CH_3$ | H | H |
| 117 | $CH_3$ | $CH_3$ | $CH_3$ | $CD_3$ | H | H |
| 118 | $CH_3$ | $CH_3$ | $CH_3$ | $CH_3$ | D | D |
| 119 | $CD_3$ | $CD_3$ | $CD_3$ | $CH_3$ | H | H |
| 120 | $CD_3$ | $CH_3$ | $CH_3$ | $CD_3$ | H | H |
| 121 | $CD_3$ | $CH_3$ | $CH_3$ | $CH_3$ | D | D |
| 122 | $CH_3$ | $CD_3$ | $CD_3$ | $CD_3$ | H | H |
| 123 | $CH_3$ | $CD_3$ | $CD_3$ | $CH_3$ | D | D |
| 124 | $CH_3$ | $CH_3$ | $CH_3$ | $CD_3$ | D | D |
| 125 | $CD_3$ | $CD_3$ | $CD_3$ | $CD_3$ | H | H |
| 126 | $CD_3$ | $CH_3$ | $CH_3$ | $CD_3$ | D | D |
| 127 | $CH_3$ | $CD_3$ | $CD_3$ | $CD_3$ | D | D |
| 128 | $CD_3$ | $CD_3$ | $CD_3$ | $CD_3$ | D | D |

In some embodiments, any atom not designated as deuterium is present at its natural isotopic abundance.

Also provided is a pyrogen-free pharmaceutical composition comprising a compound of Formula I and a pharmaceutically acceptable carrier.

In some embodiments, a pyrogen-free pharmaceutical composition further comprises a second therapeutic agent selected from an antiviral agent, an anti-infective, an immunomodulator, an antibiotic, a CCR5 receptor antagonist, a vaccine, a viral protease inhibitor, a nucleoside reverse transcriptase inhibitor and a non-nucleoside reverse transcriptase inhibitor.

In some embodiments, the second therapeutic agent is selected from one or more of darunavir, ritonavir, and etravirine.

Also provided is a method of modulating the activity of HIV integrase in an HIV-infected cell, comprising the step of contacting the cell with one or more compounds of Formula I.

Further provided is a method of treating a patient suffering from, or susceptible to, an HIV infection, comprising the step of administering to the patient in need thereof a pyrogen-free pharmaceutical composition comprising a compound of Formula I.

In some embodiments, the method includes the additional step of co-administering to the patient in need thereof a second therapeutic selected from one or more of an antiviral agent, an anti-infective, an immunomodulator, an antibiotic, a CCR5 receptor antagonist, a vaccine, a viral protease inhibitor, a nucleoside reverse transcriptase inhibitor and a non-nucleoside reverse transcriptase inhibitor.

In some embodiments, the second therapeutic agent is selected from one or more of darunavir, ritonavir, and etravirine.

DETAILED DESCRIPTION

Definitions

The terms "ameliorate" and "treat" are used interchangeably and include therapeutic and/or prophylactic treatment. Both terms mean decrease, suppress, attenuate, diminish, arrest, or stabilize the development or progression of a disease (e.g., a disease or disorder delineated herein).

"Disease" means any condition or disorder that damages or interferes with the normal function of a cell, tissue, or organ.

It will be recognized that some variation of natural isotopic abundance occurs in a synthesized compound depending upon the origin of chemical materials used in the synthesis. Thus, a preparation of raltegravir will inherently contain small amounts of deuterated and/or $^{13}C$-containing isotopologues. The concentration of naturally abundant stable hydrogen and carbon isotopes, notwithstanding this variation, is small and immaterial as compared to the degree of stable isotopic substitution of compounds of this disclosure. See, for instance, Wada E et al., Seikagaku, 1994, 66:15; Ganes L Z et al., Comp Biochem Physiol Mol Integr Physiol, 1998, 119: 725. In a compound of this disclosure, when a particular position is designated as having deuterium, it is understood that the abundance of deuterium at that position is substantially greater than the natural abundance of deuterium, which is 0.015%. Also unless otherwise stated, when a position is designated specifically as "D" or "deuterium", the position is understood to have deuterium at an abundance that is at least 3340 times greater than the natural abundance of deuterium, which is 0.015% (i.e., at least 50.1% incorporation of deuterium).

The term "isotopic enrichment factor" as used herein means the ratio between the isotopic abundance of D at a specified position in a compound of this disclosure and the naturally occurring abundance of that isotope. The natural abundance of deuterium is 0.015%.

In other embodiments, a compound of this disclosure has an isotopic enrichment factor for each deuterium present at a site designated as a potential site of deuteration on the compound of at least 3500 (52.5% deuterium incorporation), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). It is understood that the isotopic enrichment factor of each deuterium present at a site designated as a site of deuteration is independent of other deuterated sites. For example, if there are two sites of deuteration on a compound one site could be deuterated at 52.5% while the other could be deuterated at 75%. The resulting compound would be considered to be a compound wherein the isotopic enrichment factor is at least 3500 (52.5%).

The term "isotopologue" refers to a species that has the same chemical structure and formula as a specific compound of this disclosure, with the exception of the isotopic composition at one or more positions, e.g., H vs. D, and/or the level of isotopic enrichment at one or more positions.

The term "compound," as used herein, refers to a collection of molecules having an identical chemical structure, except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this disclosure will depend upon a number of factors including the isotopic purity of deuterated reagents used to make the compound and the efficiency of incorporation of deuterium in the various synthesis steps used to prepare the compound. However, as set forth above the relative amount of such isotopologues will be less than 49.9% of the compound. The term "compound," as used herein, is also intended to include any salts, solvates or hydrates thereof.

A salt of a compound of this disclosure is formed between an acid and a basic group of the compound, such as an amino functional group, or a base and an acidic group of the compound, such as a carboxyl functional group. According to another embodiment, the compound is a pharmaceutically acceptable acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this disclosure. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

As used herein, the term "hydrate" means a compound which further includes a stoichiometric or non-stoichiometric amount of water bound by non-covalent intermolecular forces.

As used herein, the term "solvate" means a compound which further includes a stoichiometric or non-stoichiometric amount of solvent such as water, acetone, ethanol, methanol, dichloromethane, 2-propanol, or the like, bound by non-covalent intermolecular forces.

The compounds of the present disclosure (e.g., compounds of Formula I), may contain an asymmetric carbon atom, for example, as the result of deuterium substitution or otherwise. As such, compounds of this disclosure can exist as either individual enantiomers, or mixtures of the two enantiomers. Accordingly, a compound of the present disclosure will include both racemic mixtures, and also individual respective stereoisomers that are substantially free from another possible stereoisomer. The term "substantially free of other stereoisomers" as used herein means less than 25% of other stereoisomers, preferably less than 10% of other stereoisomers, more preferably less than 5% of other stereoisomers and most preferably less than 2% of other stereoisomers, or less than "X"% of other stereoisomers (wherein X is a number between 0 and 100, inclusive) are present. Methods of obtaining or synthesizing an individual enantiomer for a given compound are well known in the art and may be applied as practicable to final compounds or to starting material or intermediates.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"D" refers to deuterium.

"Stereoisomer" refers to both enantiomers and diastereomers.

Throughout this specification, a variable may be referred to generally (e.g., "each R") or may be referred to specifically (e.g., $R^1$, $R^{2a}$, $R^{2b}$, etc.). Unless otherwise indicated, when a variable is referred to generally, it is meant to include all specific embodiments of that particular variable.

Therapeutic Compounds

The present disclosure provides a compound of Formula I:

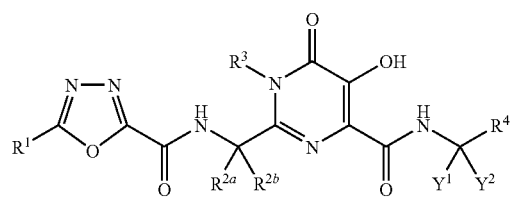

or a pharmaceutically acceptable salt, solvate, or hydrate thereof, wherein:

each of $R^1$, $R^{2a}$, $R^{2b}$, and $R^3$ is independently selected from $CH_3$, $CDH_2$, $CD_2H$, and $CD_3$;

$Y^1$ and $Y^2$ are each independently selected from H or D;

$R^4$ is selected from:

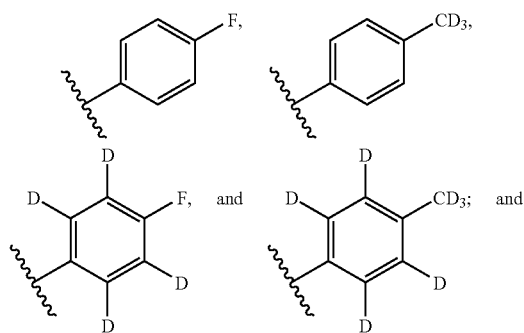

when each R is CH₃, at least one Y is D.

In one embodiment, each of $R^1$, $R^{2a}$, $R^{2b}$, and $R^3$ is independently selected from $CH_3$, and $CD_3$.

In another embodiment, $R^4$ is selected from

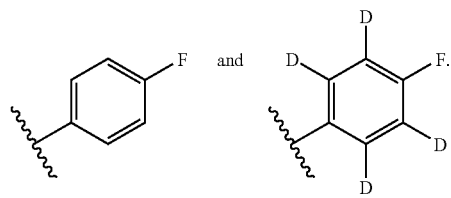

In another embodiment, $Y^1$ and $Y^2$ are the same.

In yet another embodiment $R^{2a}$ and $R^{2b}$ are the same. In a particular embodiment, $R^{2a}$ and $R^{2b}$ are the same and are selected from $CH_3$ and $CD_3$.

According to another embodiment, $R^4$ is selected from

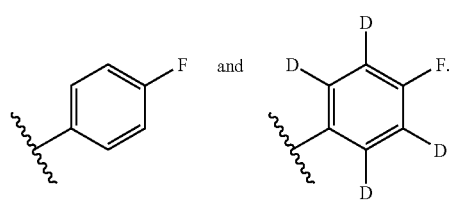

Examples of specific compounds are shown in Tables 1 and 2 below.

TABLE 1

Specific Compounds of Formula I where $R^4$ is [structure: 4-fluorophenyl]

| Compound | $R^1$ | $R^{2a}$ | $R^{2b}$ | $R^3$ | $Y^1$ | $Y^2$ |
|---|---|---|---|---|---|---|
| 101 | CD₃ | CH₃ | CH₃ | CH₃ | H | H |
| 102 | CH₃ | CD₃ | CD₃ | CH₃ | H | H |
| 103 | CH₃ | CH₃ | CH₃ | CD₃ | H | H |
| 104 | CH₃ | CH₃ | CH₃ | CH₃ | D | D |
| 105 | CD₃ | CD₃ | CD₃ | CH₃ | H | H |
| 106 | CD₃ | CH₃ | CH₃ | CD₃ | H | H |
| 107 | CD₃ | CH₃ | CH₃ | CH₃ | D | D |
| 108 | CH₃ | CD₃ | CD₃ | CD₃ | H | H |
| 109 | CH₃ | CD₃ | CD₃ | CH₃ | D | D |

TABLE 1-continued

Specific Compounds of Formula I where $R^4$ is [structure: 4-fluorophenyl]

| Compound | $R^1$ | $R^{2a}$ | $R^{2b}$ | $R^3$ | $Y^1$ | $Y^2$ |
|---|---|---|---|---|---|---|
| 110 | CH₃ | CH₃ | CH₃ | CD₃ | D | D |
| 111 | CD₃ | CD₃ | CD₃ | CD₃ | H | H |
| 112 | CD₃ | CH₃ | CH₃ | CD₃ | D | D |
| 113 | CH₃ | CD₃ | CD₃ | CD₃ | D | D |
| 114 | CD₃ | CD₃ | CD₃ | CD₃ | D | D |

TABLE 2

Specific Compounds of Formula I where $R^4$ is [deuterated fluorophenyl structure]

| Compound | $R^1$ | $R^{2a}$ | $R^{2b}$ | $R^3$ | $Y^1$ | $Y^2$ |
|---|---|---|---|---|---|---|
| 115 | CD₃ | CH₃ | CH₃ | CH₃ | H | H |
| 116 | CH₃ | CD₃ | CD₃ | CH₃ | H | H |
| 117 | CH₃ | CH₃ | CH₃ | CD₃ | H | H |
| 118 | CH₃ | CH₃ | CH₃ | CH₃ | D | D |
| 119 | CD₃ | CD₃ | CD₃ | CH₃ | H | H |
| 120 | CD₃ | CH₃ | CH₃ | CD₃ | H | H |
| 121 | CD₃ | CH₃ | CH₃ | CH₃ | D | D |
| 122 | CH₃ | CD₃ | CD₃ | CD₃ | H | H |
| 123 | CH₃ | CD₃ | CD₃ | CH₃ | D | D |
| 124 | CH₃ | CH₃ | CH₃ | CD₃ | D | D |
| 125 | CD₃ | CD₃ | CD₃ | CD₃ | H | H |
| 126 | CD₃ | CH₃ | CH₃ | CD₃ | D | D |
| 127 | CH₃ | CD₃ | CD₃ | CD₃ | D | D |
| 128 | CD₃ | CD₃ | CD₃ | CD₃ | D | D |

In another set of embodiments, any atom not designated as deuterium in any of the embodiments set forth above is present at its natural isotopic abundance.

In another set of embodiments, the compound of Formula I is isolated or purified, e.g., the compound of Formula I is present at a purity of at least 50.1% by weight (e.g., at least 52.5%, 54%, 55%, 60%, 65%, 70%, 75%, 80%, 85%, 90%, 95%, 97%, 98%, 98.5%, 99%, 99.5% or 99.9%) of the total amount of isotopologues of Formula I present, respectively. Thus, in some embodiments, a composition comprising a compound of Formula I can include a distribution of isotopologues of the compound, provided at least 50.1% of the isotopologues by weight are the recited compound.

In some embodiments, any position in the compound of Formula I designated as having D has a minimum deuterium incorporation of at least 50.1% (e.g., at least 52.5%, at least 60%, at least 67.5%, at least 75%, at least 82.5%, at least 90%, at least 95%, at least 97%, at least 99%, or at least 99.5%) at the designated position(s) of the compound of Formula I. Thus, in some embodiments, a composition comprising a compound of Formula I can include a distribution of isotopologues of the compound, provided at least 50.1% of the isotopologues include a D at the designated position(s).

In some embodiments, a compound of Formula I is "substantially free of" other isotopologues of the compound, e.g., less than 49.9%, less than 25%, less than 10%, less than 5%, less than 2%, less than 1%, or less than 0.5% of other isotopologues are present.

The synthesis of compounds of Formula I can be readily achieved by synthetic chemists of ordinary skill. Relevant procedures and intermediates are disclosed, for instance in PCT publication No. WO2006060712.

Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure. Certain intermediates can be used with or without purification (e.g., filtration, distillation, sublimation, crystallization, trituration, solid phase extraction, and chromatography).

Exemplary Synthesis

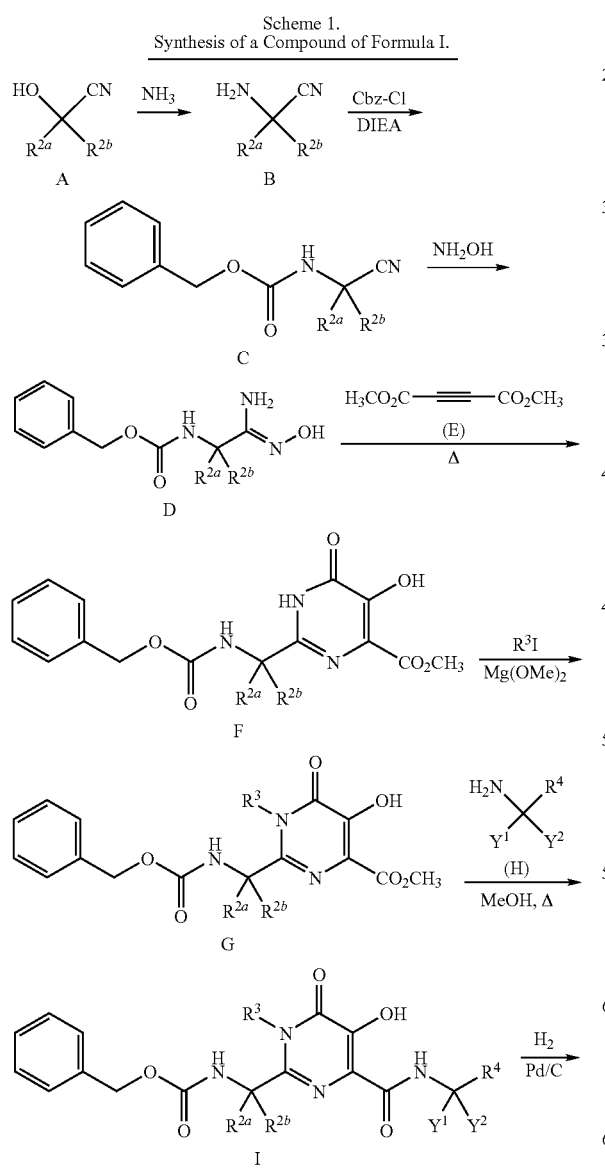

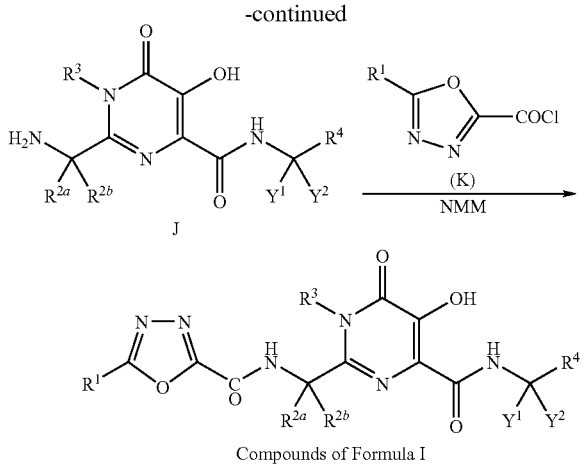

A convenient method for synthesizing compounds of Formula I is depicted in Scheme 1. Compound A is first treated with ammonia to provide B, which is subsequently treated with Cbz-chloride in the presence of diisopropylethylamine to provide carbamate C. The deuterated version of A is prepared from commercially available $D_6$-acetone and potassium cyanide as described by Horino, Y et al., Chem Eur J, 2003, 9(11):2419-2438. C is then allowed to react with hydroxylamine to provide D, which is condensed with dimethyl acetylenedicarboxylate (E) and cyclized to the pyrimidone F. The pyrimidone F is N-alkylated with iodomethane or $D_3$-iodomethane in the presence of magnesium methoxide to provide G, which is converted to amide I by reaction with H. The appropriately deuterated analogs of formula H can be prepared as shown below in Scheme 2. The Cbz group is removed by catalytic hydrogenation to yield J, which is then acylated with K in the presence of N-methylmorpholine to provide compounds of formula I.

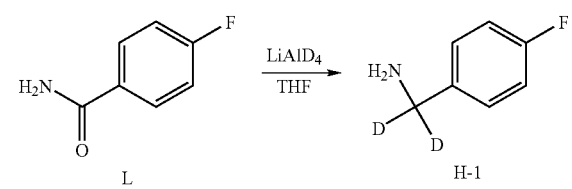

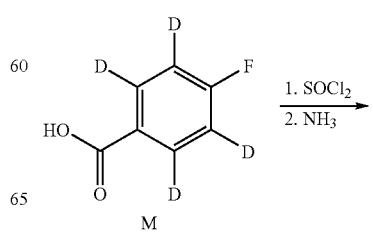

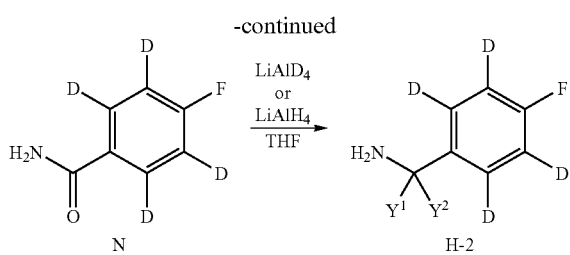

Schemes 2a and 2b depict the synthesis of alternative $R^4$ moieties that may be used in Scheme 1. In Scheme 2a, amide L is reduced to a primary amine H-1 with lithium aluminum deuteride as described for lithium aluminum hydride by Tachibana, Y et al., J Org Chem, 2006, 71(14):5093-5104. H-1 is then used as shown in Scheme 1.

As depicted in Scheme 2b, to produce the D4-aryl version of H (H-2), commercially available M is converted to the acid chloride with thionyl chloride and then treated with ammonia to provide the amide N (see Sardashti, M et al., J Phys Chem, 1988, 92(16):4620-4632). The amide N is converted to the appropriately deuterated amine H-2 using lithium aluminum deuteride or lithium aluminum hydride.

Scheme 3.
Synthesis of Compound K.

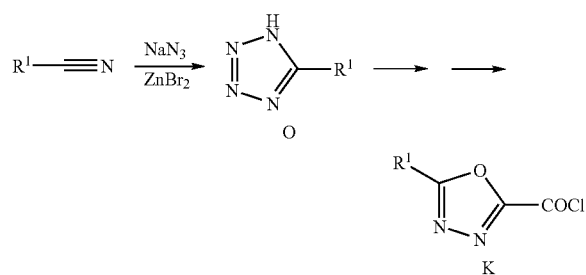

Compound K (cf. Scheme 1) is prepared as provided in Scheme 3 from the deuterated tetrazole O, which is produced from commercially available deuterated acetonitrile as described by Demko, Z P et al., J Org Chem, 2001, 66(24): 7945-7950 as shown in Scheme 3. The tetrazole is then converted to K using the procedures disclosed in International Publication Number WO2006060712.

The specific approaches and compounds shown above are not intended to be limiting. The chemical structures in the schemes herein depict variables that are hereby defined commensurately with chemical group definitions (moieties, atoms, etc.) of the corresponding position in the compound formulae herein, whether identified by the same variable name (i.e., $R^1$, $R^2$, $R^3$, etc.) or not. The suitability of a chemical group in a compound structure for use in the synthesis of another compound is within the knowledge of one of ordinary skill in the art. Additional methods of synthesizing compounds of Formula I and their synthetic precursors, including those within routes not explicitly shown in schemes herein, are within the means of chemists of ordinary skill in the art. Methods for optimizing reaction conditions and, if necessary, minimizing competing by-products, are known in the art. In addition to the synthetic references cited herein, reaction schemes and protocols may be determined by the skilled artisan by use of commercially available structure-searchable database software, for instance, SciFinder® (CAS division of the American Chemical Society), STN® (CAS division of the American Chemical Society), CrossFire Beilstein® (Elsevier MDL), or internet search engines such as Google® or keyword databases such as the US Patent and Trademark Office text database.

The methods described herein may also additionally include steps, either before or after the steps described specifically herein, to add or remove suitable protecting groups in order to ultimately allow synthesis of the compounds herein. In addition, various synthetic steps may be performed in an alternate sequence or order to give the desired compounds. Synthetic chemistry transformations and protecting group methodologies (protection and deprotection) useful in synthesizing the applicable compounds are known in the art and include, for example, those described in Larock R, *Comprehensive Organic Transformations*, VCH Publishers (1989); Greene T W et al., *Protective Groups in Organic Synthesis*, 3$^{rd}$ Ed., John Wiley and Sons (1999); Fieser L et al., *Fieser and Fieser's Reagents for Organic Synthesis*, John Wiley and Sons (1994); and Paquette L, ed., *Encyclopedia of Reagents for Organic Synthesis*, John Wiley and Sons (1995) and subsequent editions thereof.

Combinations of substituents and variables envisioned by this disclosure are only those that result in the formation of stable compounds.

Compositions

The disclosure also provides pyrogen-free compositions comprising an effective amount of a compound of Formula I (e.g., including any of the formulae herein), or a pharmaceutically acceptable salt, solvate, or hydrate of said compound; and an acceptable carrier. Preferably, a composition of this disclosure is formulated for pharmaceutical use ("a pharmaceutical composition"), wherein the carrier is a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of the disclosure include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington's Pharmaceutical Sciences, Mack Publishing Company, Philadelphia, Pa. (17th ed. 1985).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present disclosure suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this disclosure may be administered in the form of suppositories for rectal administration. These compositions can be prepared by mixing a compound of this disclosure with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this disclosure may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g. U.S. Pat. No. 6,803,031.

Topical administration of the pharmaceutical compositions of this disclosure is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of this disclosure include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this disclosure may also be topically applied to the lower intestinal tract by rectal suppository formulation or in a suitable enema formulation. Topically-transdermal patches and iontophoretic administration are also included in this disclosure.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

Thus, according to yet another embodiment, the compounds of this disclosure may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the disclosure provides a method of coating an implantable medical device comprising the step of contacting said device with the coating composition described above. It will be obvious to those skilled in the art that the coating of the device will occur prior to implantation into a mammal.

According to another embodiment, the disclosure provides a method of impregnating an implantable drug release device comprising the step of contacting said drug release device with a compound or composition of this disclosure. Implantable drug release devices include, but are not limited to, biodegradable polymer capsules or bullets, non-degradable, diffusible polymer capsules and biodegradable polymer wafers.

According to another embodiment, the disclosure provides an implantable medical device coated with a compound or a composition comprising a compound of this disclosure, such that said compound is therapeutically active.

According to another embodiment, the disclosure provides an implantable drug release device impregnated with or containing a compound or a composition comprising a compound of this disclosure, such that said compound is released from said device and is therapeutically active.

Where an organ or tissue is accessible because of removal from the patient, such organ or tissue may be bathed in a medium containing a composition of this disclosure, a composition of this disclosure may be painted onto the organ, or a composition of this disclosure may be applied in any other convenient way.

In another embodiment, a composition of this disclosure further comprises a second therapeutic agent. The second therapeutic agent may be selected from any compound or therapeutic agent known to have or that demonstrates advantageous properties when administered with an HIV integrase inhibitor. Such agents include those described in detail in WO 2005/087767, WO 2005/087768, and WO 2006/107478.

In certain embodiments, the second therapeutic agent is any one or more of an antiviral agent (e.g., acyclovir, ganciclovir, or famciclovir), anti-infective, immunomodulator (e.g., granulocyte macrophage colony stimulating factor, gamma interferon, and IL-2), antibiotic (e.g., clindamycin, fluconazole, pentamidine, and trimethoprim), CCR5 receptor antagonist (e.g., maraviroc, vicriviroc, PRO-140 and TAK-220), vaccine, HIV protease inhibitor (e.g., indinavir, ritonavir, darunavir or nelfinavir), nucleoside reverse transcriptase inhibitor or non-nucleoside reverse transcriptase inhibitor (e.g., etravirine, azidothymidine (AZT) or efavirenz).

In one embodiment, the second therapeutic agent is selected from one or more of darunavir, ritonavir, and etravirine.

In another embodiment, the disclosure provides separate dosage forms of a compound of this disclosure and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the disclosure, the compound of the present disclosure is present in an effective amount. As used herein, the term "effective amount" refers to an amount which, when administered in a proper dosing regimen, is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy.

The interrelationship of dosages for animals and humans (based on milligrams per meter squared of body surface) is described in Freireich et al., (1966) Cancer Chemother. Rep 50: 219. Body surface area may be approximately determined from height and weight of the patient. See, e.g., Scientific Tables, Geigy Pharmaceuticals, Ardsley, N.Y., 1970, 537.

In one embodiment, an effective amount of a compound of this disclosure can range from about 0.01 to about 500 mg/kg body weight per day orally in a single dose or in divided doses. Another preferred dosage range is about 0.1 to about 100 mg/kg body weight per day orally in single or divided doses. A more specific dosage range is from about 1 to about 25 mg/kg body weight. For oral administration, the compositions can be provided in the form of tablets or capsules containing about 1.0 to about 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the patient to be treated.

Effective doses will also vary, as recognized by those skilled in the art, depending on the diseases treated, the severity of the disease, the route of administration, the sex, age and general health condition of the patient, excipient usage, the possibility of co-usage with other therapeutic treatments such as use of other agents and the judgment of the treating physician. For example, guidance for selecting an effective dose can be determined by reference to the prescribing information for raltegravir.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

It is expected that some of the second therapeutic agents referenced above will act synergistically with the compounds of this disclosure. When this occurs, it will allow the effective dosage of the second therapeutic agent and/or the compound of this disclosure to be reduced from that required in a monotherapy. This has the advantage of minimizing toxic side effects of either the second therapeutic agent of a compound of this disclosure, synergistic improvements in efficacy, improved ease of administration or use and/or reduced overall expense of compound preparation or formulation.

Methods of Treatment

In another embodiment, the disclosure provides a method of modulating the activity of HIV integrase in an HIV-infected cell, comprising contacting the cell with one or more compounds of Formula I herein.

According to another embodiment, the disclosure provides a method of treating a patient suffering from, or susceptible to, an HIV infection and the prevention, treatment or the delay in the onset of consequent pathological conditions such as AIDS. This includes, but is not limited to, treatment of a wide range of states of HIV infection: AIDS, ARC (AIDS related complex), both symptomatic and asymptomatic, and actual or potential exposure to HIV. For example, the compounds of this disclosure are useful in treating infection by HIV after suspected past exposure to HIV by such means as blood transfusion, exchange of body fluids, bites, accidental needle stick, or exposure to patient blood during surgery.

Methods delineated herein also include those wherein the patient is identified as in need of a particular stated treatment. Identifying a patient in need of such treatment can be in the judgment of a patient or a health care professional and can be subjective (e.g. opinion) or objective (e.g. measurable by a test or diagnostic method).

In another embodiment, any of the above methods of treatment comprises the further step of co-administering to said patient one or more second therapeutic agents. The choice of second therapeutic agent may be made from any second therapeutic agent known to be useful for co-administration with raltegravir. The choice of second therapeutic agent is also dependent upon the particular disease or condition to be treated. Examples of second therapeutic agents that may be employed in the methods of this disclosure are those set forth above for use in combination compositions comprising a compound of this disclosure and a second therapeutic agent.

In particular, the combination therapies of this disclosure include co-administering a compound of Formula I and a second therapeutic agent selected from one or more of darunavir, ritonavir, and etravirine.

The term "co-administered" as used herein means that the second therapeutic agent may be administered together with a compound of this disclosure as part of a single dosage form (such as a composition of this disclosure comprising a compound of the disclosure and an second therapeutic agent as described above) or as separate, multiple dosage forms. Alternatively, the additional agent may be administered prior to, consecutively with, or following the administration of a compound of this disclosure. In such combination therapy treatment, both the compounds of this disclosure and the second therapeutic agent(s) are administered by conventional methods. The administration of a composition of this disclosure, comprising both a compound of the disclosure and a second therapeutic agent, to a patient does not preclude the separate administration of that same therapeutic agent, any other second therapeutic agent or any compound of this disclosure to said patient at another time during a course of treatment.

Effective amounts of these second therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the disclosure, where a second therapeutic agent is administered to a subject, the effective amount of the compound of this disclosure is less than its effective amount would be where the second therapeutic agent is not administered. In another embodiment, the effective amount of the second therapeutic agent is less than its effective amount would be where the compound of this disclosure is not administered. In this way, undesired side effects associated with high doses of either agent may be minimized. Other potential advantages (including without limitation improved dosing regimens and/or reduced drug cost) will be apparent to those of skill in the art.

In yet another aspect, the disclosure provides the use of a compound of Formula I alone or together with one or more of the above-described second therapeutic agents in the manufacture of a medicament, either as a single composition or as separate dosage forms, for treatment or prevention in a patient of a disease, disorder or symptom set forth above. Another aspect of the disclosure is a compound of Formula I for use in the treatment or prevention in a patient of a disease, disorder or symptom thereof delineated herein.

Diagnostic Methods and Kits

The compounds and compositions of this disclosure are also useful as reagents in methods for determining the concentration of raltegravir in solution or biological sample such as plasma, examining the metabolism of raltegravir and other analytical studies.

According to one embodiment, the disclosure provides a method of determining the concentration, in a solution or a biological sample, of raltegravir, comprising the steps of:

a) adding a known concentration of a compound of Formula I to the solution of biological sample;

b) subjecting the solution or biological sample to a measuring device that distinguishes raltegravir from a compound of Formula I;

c) calibrating the measuring device to correlate the detected quantity of the compound of Formula I with the known concentration of the compound of Formula I added to the biological sample or solution; and d) measuring the quantity of raltegravir in the biological sample with said calibrated measuring device; and e) determining the concentration of raltegravir in the solution of sample using the correlation between detected quantity and concentration obtained for a compound of Formula I.

Measuring devices that can distinguish raltegravir from the corresponding compound of Formula I include any measuring device that can distinguish between two compounds that differ from one another in isotopic abundance. Exemplary measuring devices include a mass spectrometer, NMR spectrometer, or IR spectrometer.

In another embodiment, a method for determining the amount of raltegravir in a solution or a biological sample is provided, comprising:

a) adding a known amount of a compound of Formula I to the solution or biological sample;

b) detecting at least one signal for a compound of Formula I and at least one signal for raltegravir in a measuring device that is capable of distinguishing the two compounds;

c) correlating the at least one signal detected for a compound of Formula I with the known amount of the compound of Formula I added to the solution or the biological sample; and d) determining the amount of raltegravir in the solution or biological sample using the correlation between the at least one signal detected of the compound of Formula I and the amount added to the solution or biological sample of a compound of Formula I.

In another embodiment, the disclosure provides a method of evaluating the metabolic stability of a compound of Formula I comprising the steps of contacting the compound of Formula I with a metabolizing enzyme source for a period of time and comparing the amount of the compound of Formula I with the metabolic products of the compound of Formula I after the period of time.

In a related embodiment, the disclosure provides a method of evaluating the metabolic stability of a compound of Formula I in a patient following administration of the compound of Formula I. This method comprises the steps of obtaining a serum, blood, tissue, urine or feces sample from the patient at a period of time following the administration of the compound of Formula I to the subject; and comparing the amount of the compound of Formula I with the metabolic products of the compound of Formula I in the serum, blood, tissue, urine or feces sample.

The present disclosure also provides kits for use to treat HIV infection. These kits comprise (a) a pharmaceutical composition comprising a compound of Formula I or a salt, hydrate, or solvate thereof, wherein said pharmaceutical composition is in a container; and (b) instructions describing a method of using the pharmaceutical composition to treat an HIV infection.

The container may be any vessel or other sealed or sealable apparatus that can hold said pharmaceutical composition. Examples include bottles, ampules, divided or multi-chambered holders bottles, wherein each division or chamber comprises a single dose of said composition, a divided foil packet wherein each division comprises a single dose of said composition, or a dispenser that dispenses single doses of said composition. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle, which is in turn contained within a box. In one embodiment, the container is a blister pack.

The kits of this disclosure may also comprise a device to administer or to measure out a unit dose of the pharmaceutical composition. Such device may include an inhaler if said composition is an inhalable composition; a syringe and needle if said composition is an injectable composition; a syringe, spoon, pump, or a vessel with or without volume markings if said composition is an oral liquid composition; or any other measuring or delivery device appropriate to the dosage formulation of the composition present in the kit.

In certain embodiment, the kits of this disclosure may comprise in a separate vessel of container a pharmaceutical composition comprising a second therapeutic agent, such as one of those listed above for use for co-administration with a compound of this disclosure.

EXAMPLES

Example 1

Synthesis of Intermediate (4-Fluorophenyl-$d_4$)-(methan-$d_2$)-amine hydrochloride (14)

Intermediate 14 was prepared as outlined in Scheme 4 below, and Scheme 2 above. Details of the synthesis are set forth below.

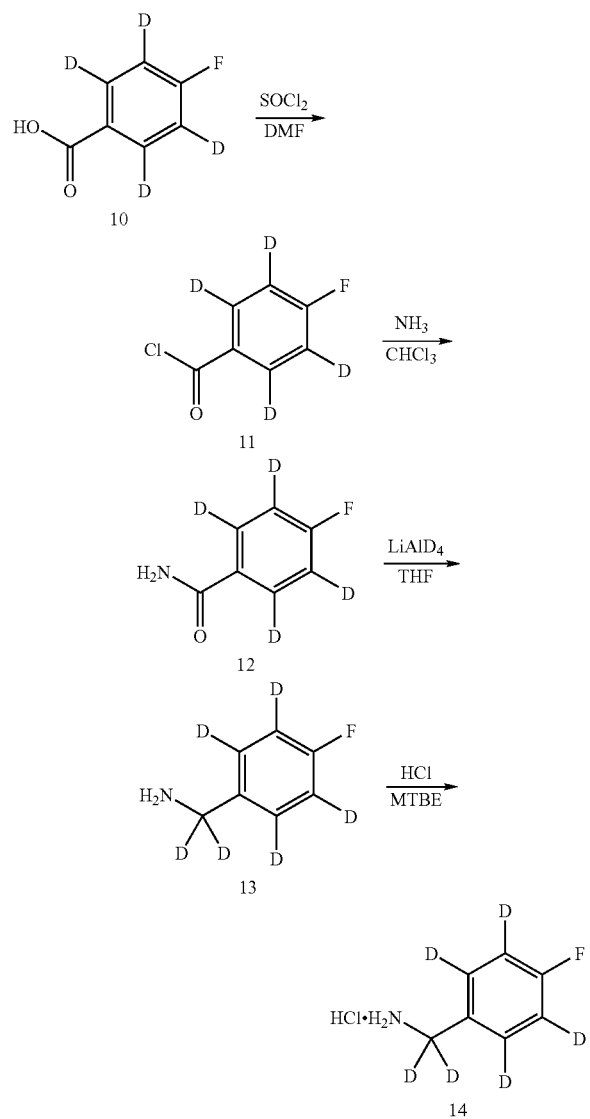

Synthesis of 4-Fluorobenzoyl chloride-$d_4$ (11). A solution of 4-fluorobenzoic acid-$d_4$ 10 (99 atom % D) 1.00 g, 6.94 mmol), thionyl chloride (6.60 g, 55.5 mmol) and DMF (cat.) was stirred under reflux conditions for 24 h. The reaction was cooled to room temperature (rt) and toluene (10 mL) was added. The solution was concentrated in vacuo and taken directly to the next step.

Synthesis of 4-Fluorobenzamide-$d_4$ (12). To a solution of the acid chloride 11 in $CHCl_3$ (4.0 mL) was added with stirring 25% aqueous (aq) $NH_3$ (4.0 mL), resulting in the formation of a white precipitate. The reaction mixture was stirred at rt for 48 hours (h). The precipitate was filtered and washed with water to give amide 12 as a white solid (440 mg). The filtrate was extracted with $CHCl_3$ (2×20 mL), the combined organic layers were washed with brine and concentrated in vacuo to give additional product (125 mg, combined yield 57% for 2 steps). $^1H$ NMR (300 MHz, $CDCl_3$): δ 5.6-6.2 (2H, bs). MS (M+H): 144.

Synthesis of (4-Fluorophenyl-$d_4$)-(methan-$d_2$)-amine (13). To a solution of amide 12 (5.00 g, 34.9 mmol) in THF (70 mL) stirring at 0° C. under $N_2$ was added $LiAlD_4$ (98 atom % D) (4.40 g, 105 mmol). The reaction mixture was stirred at reflux for 36 h, cooled to rt, then further cooled to 5° C., at which time it was quenched with $D_2O$ (4.5 mL), 15% NaOH in $D_2O$ (10 mL) and $D_2O$ (10 mL) in that order. The resulting solids were filtered and washed with EtOAc. The filtrate was concentrated in vacuo and dried by azeotropic distillation with toluene (3 times) to give the product as a yellow liquid (4.60 g, quantitative). $^1H$ NMR (300 MHz, $CDCl_3$): δ 2.17 (2H, bs). MS (M+H): 132.

Synthesis of (4-Fluorophenyl-$d_4$)-(methan-$d_2$)-amine hydrochloride (14). To a filtered solution of amine 13 (4.60 g, 35.0 mmol) in MTBE (150 mL) at 0-5° C., was added dropwise a 1.6M solution of HCl in ether (33 mL). Instantaneous precipitation of a white solid resulted. After addition was complete, the reaction was stirred at 0-5° C. for 1 h then was filtered. The resulting white, pasty precipitate was washed with ether (5×50 mL) to give 14 as a white powder (3.80 g, 65%). $^1H$ NMR (300 MHz, DMSO-$d_6$): δ 8.62 (3H, bs). MS (M+H): 132.

Example 2

Synthesis of Intermediate Potassium 5-(methyl-$d_3$)-1,3,4-oxadiazole-2-carboxylate (19a)

Intermediate 19a was prepared as outlined in Scheme 5 below. Details of the synthesis are set forth below.

Scheme 5.

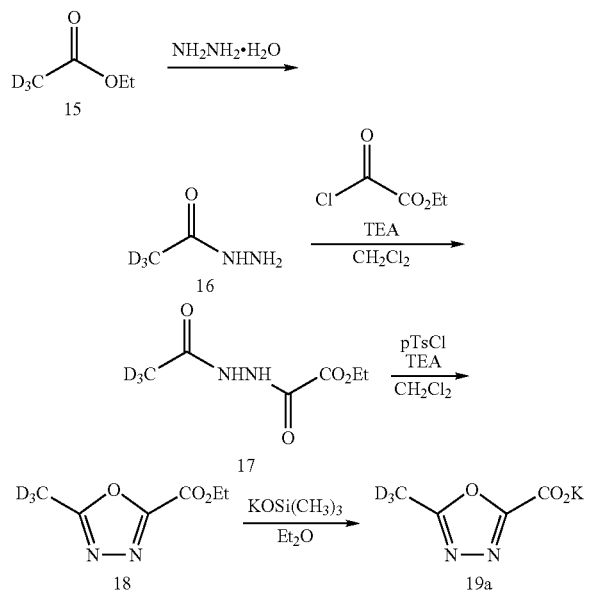

Synthesis of Acetohydrazide-$d_3$ (16). A mixture of ethyl (acetate-$d_3$) 15 (99.5 atom % D) (5.00 g, 54.9 mmol) and hydrazine hydrate (35.0 mL, 72 mmol) was heated to reflux and stirred for 15 h. The reaction mixture was concentrated in vacuo and taken directly to the next step. MS (M+H): 78.1.

Synthesis of Ethyl 2-(2-(acetyl-$d_3$)hydrazinyl)-2-oxoacetate (17). To a solution of the hydrazide 16 (4.20 g, 53.8 mmol) in $CH_2Cl_2$ (25 mL) stirring at 0° C. under $N_2$, was added triethylamine (9.8 mL, 69.9 mmol) followed by ethyl chlorooxoacetate (7.2 mL, 64.6 mmol) over 1 h. The reaction mixture was then stirred at rt for 8 h. Ethyl acetate was added to the reaction mixture and the salts were removed by filtration. The filtrate was concentrated in vacuo and the residue was purified by column chromatography using a gradient of 5-15% EtOAc/hexane to afford the product as an off-white solid (9.50 g, quantitative). MS (M+H): 178.1.

Synthesis of Ethyl 5-(methyl-$d_3$)-1,3,4-oxadiazole-2-carboxylate (18). To a solution of the oxoacetate 17 (9.50 g, 53.7 mmol) in $CH_2Cl_2$ (150 mL) was added triethylamine (9.70 mL, 69.7 mmol) and p-TsCl (11.2 g, 59.0 mmol) in three portions. The resulting reaction mixture was stirred at rt for 8 h, was diluted with $CH_2Cl_2$ and washed with water. The organic layer was dried ($Na_2SO_4$), filtered and concentrated in vacuo. The crude was purified by column chromatography using EtOAc/hexanes to give 18 as an off-white solid (2.50 g, 30%). $^1H$ NMR (400 MHz, $CDCl_3$): δ 4.45 (2H, q, J=7 Hz), 1.38 (3H, t, J=5 Hz). MS (M+H): 160.0.

Synthesis of Potassium 5-(methyl-$d_3$)-1,3,4-oxadiazole-2-carboxylate (19a). To a slurry of potassium trimethylsilanolate (1.70 g, 13.8 mmol) in ether stirring at room temperature, was added in one portion the ethyl ester 18 (2.20 g, 13.8 mmol). Immediate precipitation was observed with the color changing from white to off-white. The precipitate was removed by filtration, was washed with ether and dried to give 19a as an off-white solid (1.60 g, 69%). $^1H$ NMR (400 MHz, $D_2O$): δ No peaks observed. $^{13}C$ NMR (75 MHz, $D_2O$): δ 164.6, 162.6, 157.0, 10.2 (m). MS (M-K): 130.0.

Example 3

Synthesis of Intermediate Potassium 5-methyl-1,3,4-oxadiazole-2-carboxylate (19b)

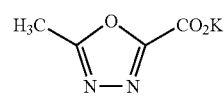

Intermediate 19b was prepared as outlined in Scheme 5 above utilizing non-deuterated starting material. Details of the synthesis are set forth below.

Synthesis of Acetohydrazide. To a solution of ethyl acetate (159 mL, 1.70 mol) in ethanol (100 ml) was added hydrazine hydrate (45 mL, 1.70 mol). The reaction mixture was stirred under reflux conditions for 4 h followed by removal of ethanol in vacuo to afford the product as a white solid (36.0 g, 30%). $^1H$ NMR (400 MHz, $CDCl_3$): δ 7.15 (1H, bs), 3.91 (2H, bs), 1.97 (3H, s). MS (M+H): 75.1.

Synthesis of Ethyl 2-(2-acetylhydrazinyl)-2-oxoacetate. To a solution of acetohydrazide (36.0 g, 486 mmol) in $CH_2Cl_2$ (250 mL) stirring at 0° C. under $N_2$, was added triethylamine (250 mL, 1.46 mol) followed by ethyl chlorooxoacetate (65.0 mL, 584 mmol) over 1 h. The reaction mixture was stirred at rt for 8 h at which time ethyl acetate was added and the salts were removed by filtration. The filtrate was concentrated in vacuo and the residue purified by column chromatography using a gradient of 5-15% EtOAc/hexane to afford the product as an off-white solid (40.0 g, 47%). $^1H$ NMR (300 MHz, $CDCl_3$): δ 9.85 (1H, bs), 9.29 (1H, bs), 4.35 (2H, q, J=7 Hz), 2.10 (3H, s), 1.36 (3H, t, J=7 Hz). MS (M+H): 175.0.

Synthesis of Ethyl 5-methyl-1,3,4-oxadiazole-2-carboxylate. To a solution of ethyl 2-(2-acetylhydrazinyl)-2-oxoacetate (0.50 g, 2.87 mmol) in $CH_2Cl_2$ (10 mL) was added triethylamine (0.53 mL, 3.73 mmol) and p-TsCl (0.65 g, 3.44 mmol) in three portions. The reaction mixture was stirred at rt for 8 h then was diluted with $CH_2Cl_2$ and washed with water.

The organic layer was dried (Na$_2$SO$_4$), filtered and concentrated in vacuo. The crude was purified by column chromatography using EtOAc/hexanes to give the title compound as an off-white solid (375 mg, 84%). $^1$H NMR (300 MHz, CDCl$_3$): δ 4.51 (2H, q, J=7 Hz), 2.65 (3H, s), 1.52 (3H, t, J=5 Hz). MS (M+H): 157.1.

Synthesis of Potassium 5-methyl-1,3,4-oxadiazole-2-carboxylate (19b). To a slurry of potassium trimethylsilanolate (411 mg, 3.20 mmol) in ether stirring at rt, was added in one portion ethyl 5-methyl-1,3,4-oxadiazole-2-carboxylate (0.50 g, 3.20 mmol). Immediate precipitation was observed with the color changing from white to off-white. The precipitate was removed by filtration, was washed with ether and dried to give the title compound as an off-white solid (580 mg, quantitative yield). $^1$H NMR (300 MHz, CDCl$_3$): δ 2.61 (3H, s). $^{13}$C NMR (75 MHz, D$_2$O): δ 166.7, 161.3, 159.3, 10.4.

Example 4

Synthesis of N-(2-(4-(4-fluoro(benzyl-d$_6$)carbamoyl)-5-hydroxy-1-(methyl-d$_3$)-6-oxo-1,6-dihydropyrimidin-2-yl)-(1,3-d$_6$-propan)-2-yl)-5-(methyl-d$_3$)-1,3,4-oxadiazole-2-carboxamide (128)

Compound 128 was prepared as outlined in Scheme 6 below and Scheme 1 above. Details of the synthesis are set forth below.

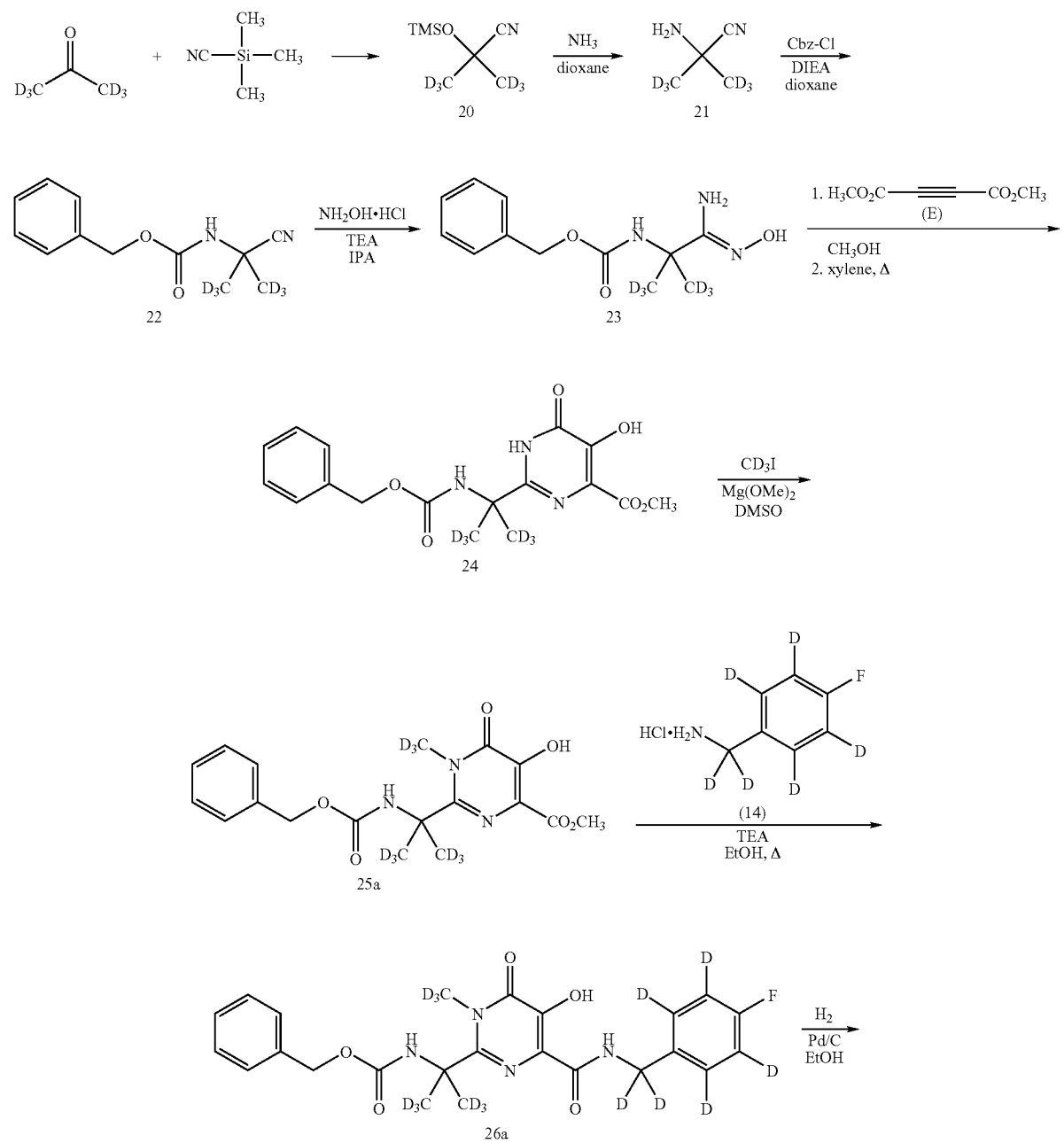

Scheme 6.

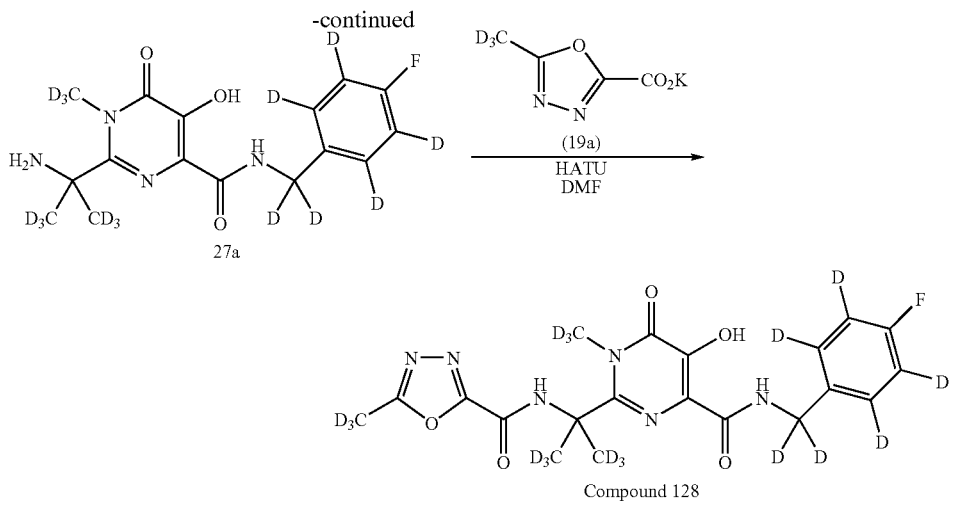

Compound 128

Synthesis of 2-(Methyl-d$_3$)-2-(trimethylsilyloxy)-(3-d$_3$-propane)nitrile (20) Trimethylsilylcyanide (25.0 g, 0.25 mol) was added to acetone-d$_6$ (99.9 atom % D) (16.0 g, 0.25 mol) and stirred at rt for 24 h. The reaction mixture was taken directly to next step.

Synthesis of 2-Amino-2-(methyl-d$_3$)-(3-d$_3$-propane)nitrile (21). The crude trimethylsiloxy product 20 from the previous step was dissolved in 1,4-dioxane (500 mL) and stirred at 0° C. Ammonia gas was bubbled through this solution for 3 h, then the reaction mixture was allowed to stir overnight at rt under an atmosphere of ammonia. The ammonia was then evaporated in vacuo and the reaction solution was taken directly to next step.

Synthesis of Benzyl 2-cyano-(1,3-d$_6$-propan)-2-ylcarbamate (22). The crude reaction solution of product 21 was dissolved in 1,4-dioxane (500 mL). To this was added dropwise with stirring CbzCl (51.2 g, 300 mmol), turning the reaction mixture turbid. N,N-diisopropylethylamine (DIEA) (42.0 g, 325 mmol) was added dropwise turning the turbid solution clear. After a brief period the reaction mixture again became turbid with the formation of two distinct layers. This mixture was stirred at rt for 2 h. MTBE was added to the reaction mixture and the solution was washed with water (3×) followed by brine. The organic layer was concentrated in vacuo to a white solid which was purified by washing with 10% MTBE/hexanes to yield product 22 (20.0 g, 35% yield for three steps). $^1$H NMR (300 MHz, CDCl$_3$): δ 7.37 (5H, bs), 5.17 (2H, s), 5.03 (1H, bs). MS (M+H): 225.

Synthesis of Benzyl 1-amino-1-(hydroxyimino)-2-(methyl-d$_3$)-(3-d$_3$-propan)-2-ylcarbamate (23). A stirring solution of aminonitrile 22 (20.0 g, 89.0 mmol) in IPA (52 mL) was warmed to 60° C. and hydroxylamine hydrochloride (50 wt %, 2.73 g, 39.3 mmol) was added dropwise followed by triethylamine (10.8 g, 106 mmol). The reaction was heated to reflux and stirred for 6 h. The solution was cooled to rt, then to 0-5° C. Hexane was added to the solution leading to the formation of a white precipitate. The precipitate was removed by filtration, dissolved in EtOAc, and the resulting organic solution was washed with water and brine. The organic layer was concentrated in vacuo to give product 23 as a white solid (23.5 g, 100%). $^1$H NMR (300 MHz, CDCl$_3$): δ 7.41 (5H, bs), 6.09 (1H, bs), 5.65 (1H, bs), 5.51 (1H, bs), 5.18 (1H, s). 5.05 (2H, s). MS (M+H): 258.1.

Synthesis of Methyl 2-(2-(benzyloxycarbonylamino)-(1,3-d$_6$-propan)-2-yl)-5-hydroxy-6-oxo-1,6-dihydropyrimidine-4-carboxylate (24). To a slurry of the amidoxime 23 (23.5 g, 91.3 mmol) in MeOH (94 mL), was added dimethylacetylene dicarboxylate E (14.0 g, 98.6 mmol) dropwise at rt. After stirring for 2 h, the reaction mixture was concentrated in vacuo and any residual MeOH was removed under high vacuum. Xylene (94 mL) was added and the reaction mixture was stirred under reflux conditions for 12 h. The reaction was cooled to 0-5° C. at which time precipitation was observed. The precitpitate was filtered and washed with 10% MeOH/MTBE to give the product 24 as an off-white solid (10.2 g, 30.4%). $^1$H NMR (300 MHz, CDCl$_3$): δ 12.0 (1H, bs), 10.7 (1H, bs), 7.29 (5H, s), 5.80 (1H, bs), 5.04 (2H, s), 4.00 (3H, s). MS (M+H): 367.9.

Synthesis of Methyl 2-(2-(benzyloxycarbonylamino)-(1,3-d$_6$-propan)-2-yl)-5-hydroxy-1-(methyl-d$_3$)-6-oxo-1,6-dihydropyrimidine-4-carboxylate (25a). To a stirred solution of pyrimidine 24 (5.40 g, 14.6 mmol) in dry DMSO (43 mL) was added a solution of Mg(OMe)$_2$ in MeOH (6-10 wt %, 36 mL) at rt. The reaction mixture was concentrated in vacuo then dried under high vacuum to remove all MeOH from the solution. The mixture was then cooled to 5° C., CD$_3$I (99.5 atom % D) (9 mL) was added and the reaction was stirred in a closed vessel at rt for 12 h. After 12 h, additional CD$_3$I (2 mL) was added to the light brown reaction mixture and stirring was continued for 4 h, at which time another portion of CD$_3$I (2 mL) was added and the reaction was stirred at rt until complete by HPLC. The reaction solution was then cooled to 5° C., 2N HCl (54 mL) was added dropwise, followed by 5% aq. NaHSO$_3$ solution (11 mL) then by water (43 mL). The resulting precipitate was filtered and washed with water (10 mL) followed by 9:1 MTBE:MeOH (50 mL) to yield the product 25a as an off-white powder (5.70 g, 82%). $^1$H NMR (500 MHz, CDCl$_3$): 10.37 (bs, 1H), 7.32 (s, 5H), 5.23 (bs, 1H), 5.03 (s, 2H), 3.99 (s, 3H). MS (M+H): 385.2.

Synthesis of Benzyl 2-(4-(4-fluoro(benzyl-d$_6$)carbamoyl)-5-hydroxy-1-(methyl-d$_3$)-6-oxo-1,6-dihydropyrimidin-2-yl)-(1,3-d$_6$-propan)-2-ylcarbamate (26a). To a solution of 25a (5.50 g, 14.3 mmol) in EtOH stirring at 0° C., was added p-fluorobenzylamine hydrochloride-d$_6$ 14 (3.60 g, 21.5 mmol) followed by triethylamine (4.34 g, 42.9 mmol). A thick suspension formed which, upon heating to 72° C., dissolved forming a clear solution. The reaction mixture was stirred for 2 h at 72° C., was cooled to 0° C. and acetic acid (HOAc) (2.2 mL) was added dropwise followed by water (26 mL). The resulting precipitate was filtered and washed with water followed by 50% EtOH/water to give product 26a as a pale pink solid (5.50 g, 80%). $^1$H NMR (400 MHz, CDCl$_3$): 10.37 (bs, 1H), 7.32 (s, 5H), 5.23 (bs, 1H), 5.03 (s, 2H), 3.49 (1H, bs).

Synthesis of 2-(2-Amino-(1,3-d$_6$-propan)-2-yl)-N-(4-fluorobenzyl-d$_6$)-5-hydroxy-1-(methyl-d$_3$)-6-oxo-1,6-dihydropyrimidine-4-carboxamide (27a). To a Parr vessel charged with 10 wt % Pd-C (35 mg), MSA (0.31 mL, 4.77 mmol) and EtOH (25 mL) was added the protected amine 26a (2.30 g, 4.77 mmol). The mixture was shaken at 50 psi hydrogen for 4 h, then was filtered through a pad of Celite and washed with EtOH. The filtrate was concentrated in vacuo, dissolved in CH$_2$Cl$_2$, washed with 1N NaOH and brine. The organic layer was concentrated in vacuo to give the title compound 27a as a pale pink solid (1.10 g, 70%). $^1$H NMR (400 MHz, DMSO-d$_6$): 10.2 (1H, bs), 7.2-5.2 (1H, bs).

Synthesis of N-(2-(4-(4-fluoro(benzyl-d$_6$)carbamoyl)-5-hydroxy-1-(methyl-d$_3$)-6-oxo-1,6-dihydropyrimidin-2-yl)-(1,3-d$_6$-propan)-2-yl)-5-(methyl-d$_3$)-1,3,4-oxadiazole-2-carboxamide (128). To a solution of 19a (0.39 g, 2.29 mmol) and amine 27a (0.50 g, 1.43 mmol) stirring in DMF (15 mL) at 0° C., was added HATU (0.92 g, 2.43 mmol). The mixture was stirred at 0° C. for 3 h. Water was added to the resultant reaction mixture and the solution was extracted repeatedly with CH$_2$Cl$_2$. The combined organic layers were washed with brine, dried over Na$_2$SO$_4$, filtered and concentrated in vacuo. The residual DMF was removed by overnight lyophilization. The crude product was purified on a combi-flash column using MeOH/CH$_2$Cl$_2$ to give Compound 128 as an off-white solid (235 mg, 22%). $^1$H NMR (400 MHz, DMSO-d$_6$): δ 12.22 (1H, s), 9.87 (1H, s), 9.10 (1H, s). MS (M+H): 463.2. HPLC (method: Luna C18 column—gradient method 5-100% ACN+0.1% TFA in 17.0 min with 3.0 min hold at 100% ACN, a 2 min hold at 70% ACN and a 3 min hold at 5% ACN; Wavelength: 254 nm): retention time: 14.65 min; 95.0% purity.

Example 5

Synthesis of N-(2-(4-(4-fluoro(benzyl-d$_6$)carbamoyl)-5-hydroxy-1-methyl-6-oxo-1,6-dihydropyrimidin-2-yl)propan-2-yl)-5-methyl-1,3,4-oxadiazole-2-carboxamide (118)

Compound 118 was prepared as outlined in Scheme 7 below. Intermediate 25b was prepared according to Scheme 6 above, utilizing non-deuterated reagents. Details of the synthesis are set forth below.

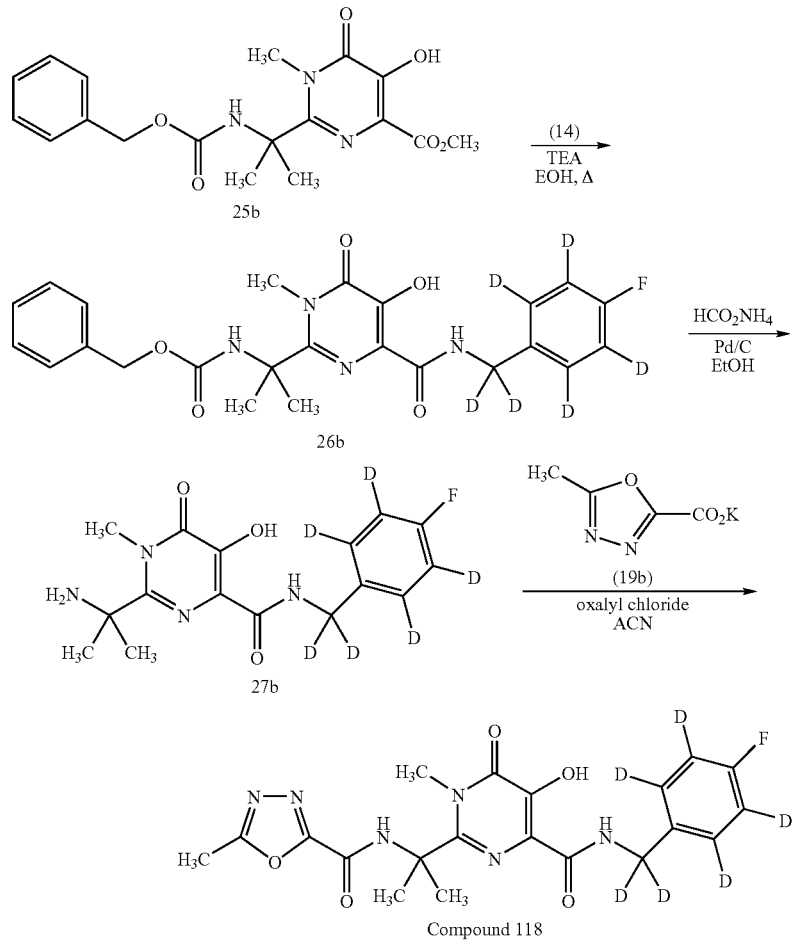

Scheme 7

Compound 118

Synthesis of Benzyl 2-(4-(4-fluoro(benzyl-d$_6$)carbamoyl)-5-hydroxy-1-methyl-6-oxo-1,6-dihydropyrimidin-2-yl)propan-2-ylcarbamate (26b). To a solution of the methylated pyrmidinone 25b (2.40 g, 6.39 mmol) in EtOH stirring at 0° C., was added p-fluorobenzylamine hydrochloride-d$_6$ 14 (1.60 g, 9.59 mmol) followed by triethylamine (1.94 g, 19.1 mmol). The resultant thick suspension cleared upon heating to 72° C., at which temperature the reaction was maintained for 2 h. The reaction was then cooled to 0° C. and HOAc (1.0 mL) was added dropwise followed by water (36 mL). The resultant precipitate was filtered and washed with water followed by 50% EtOH/water to give the product 26b as a pale pink solid (2.83 g, 94%). $^1$H NMR (300 MHz, CDCl$_3$): 11.9 (1H, bs), 7.76 (1H, bs), 7.33 (5H, s), 5.01 (2H, s), 3.65 (3H, s), 3.49 (1H, bs) 1.67 (6H, s). MS (M+H): 475.

Synthesis of 2-(2-Aminopropan-2-yl)-N-(4-fluorobenzyl-d$_6$)-5-hydroxy-1-methyl-6-oxo-1,6-dihydropyrimidine-4-carboxamide (27b). To a stirring solution of 26b (1.75 g, 3.70 mmol) in EtOH (40 mL) was added 10 wt % Pd-C (35 mg) and ammonium formate (1.16 g, 18.5 mmol). The reaction stirred under reflux conditions for 2 h then was cooled to rt, and filtered through a pad of Celite which was washed with EtOH. The combined filtrates were concentrated in vacuo to give 27b as a pale pink solid (1.18 g, 94%).

Synthesis of N-(2-(4-(4-fluoro(benzyl-d$_6$)carbamoyl)-5-hydroxy-1-methyl-6-oxo-1,6-dihydropyrimidin-2-yl)propan-2-yl)-5-methyl-1,3,4-oxadiazole-2-carboxamide (118). To a stirring slurry of 19b (0.43 g, 2.60 mmol) in acetonitrile (4.0 mL) was added a drop of DMF. The reaction mixture was cooled to 0° C., oxalyl chloride (0.22 mL, 2.50 mmol) was added over 20 min and the mixture was stirred at 0° C. for 2 h. In a separate round bottom flask a solution of 27b (0.40 g, 1.17 mmol) in THF (12 mL) was cooled to 0° C. and NMM (0.31 mL, 2.81 mmol) was added with stirring. The resultant slurry was stirred for 10 min at which time the previously prepared acid chloride solution was added over 20 min while maintaining the reaction at 0° C. The reaction mixture was then stirred at 0° C. for 2 h. The resulting yellow slurry was concentrated in vacuo, dissolved in CH$_2$Cl$_2$, washed with water (3 times) followed by brine, dried over Na$_2$SO$_4$, filtered and concentrated in vacuo. The crude product was purified by p-TLC using MeOH/CH$_2$Cl$_2$ to give Compound 118 as an off-white solid (81.0 mg, 16%). $^1$H NMR (300 MHz, DMSO-d$_6$): δ 12.21 (1H, s), 9.87 (1H, s), 9.05 (1H, s), 3.42 (3H, s), 2.55 (3H, s). MS (M+H): 451.2. HPLC (method: Luna C18 column—gradient method 5-100% ACN+0.1% TFA in 17.0 min with 3.0 min hold at 100% ACN, a 2 min hold at 70% ACN and a 3 min hold at 5% ACN; Wavelength: 254 nm): retention time: 14.65 min; 97.5% purity.

Example 6

Synthesis of N-(2-(4-(4-fluorobenzylcarbamoyl)-5-hydroxy-1-(methyl-d$_3$)6-oxo-1,6-dihydropyrimidin-2-yl)-(1,3-d$_6$-propan)-2-yl)-5-methyl-1,3,4-oxadiazole-2-carboxamide (108)

Compound 108 was prepared as outlined in Scheme 8 below. Intermediate 25a was prepared according to Scheme 6 above. Details of the synthesis are set forth below.

Scheme 8.

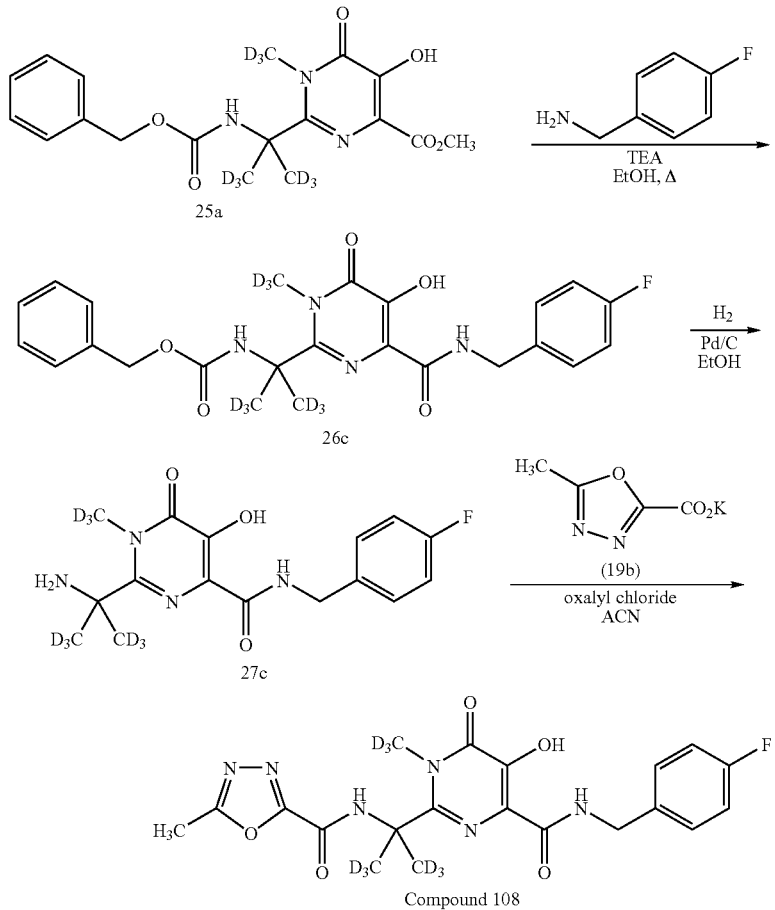

Synthesis of Benzyl 2-(4-(4-fluorobenzylcarbamoyl)-5-hydroxy-1-(methyl-d₃)-6-oxo-1,6-dihydropyrimidin-2-yl)-(1,3-d₆-propan)-2-ylcarbamate (26c). To a solution of 25a (2.50 g, 6.50 mmol) in EtOH stirring at 0° C., was added p-fluorobenzylamine (1.80 g, 14.3 mmol). The resultant thick suspension cleared upon heating to 72° C., at which temperature the reaction was maintained for 2 h. The mixture was then cooled to 0° C. and HOAc (0.8 mL) was added dropwise followed by water (10 mL). The resultant precipitate was filtered and washed with water followed by 50% EtOH/water to give 26c as a pale pink solid (2.92 g, 94%).

Synthesis of 2-(2-Amino-(1,3-d₆-propan)-2-yl)-N-4-fluorobenzyl-5-hydroxy-1-(methyl-d₃)-6-oxo-1,6-dihydropyrimidine-4-carboxamide (27c). To a Parr vessel charged with 10 wt % Pd-C (35 mg), MSA (0.4 mL, 6.00 mmol) and EtOH (20 mL) was added 26c (2.90 g, 6. mmol). The reaction mixture was shaken under 50 psi of hydrogen for 4 h. The mixture was filtered through a pad of Celite which was then washed with EtOH. The filtrate was concentrated in vacuo, dissolved in CH₂Cl₂ and the organic solution was washed with 1N NaOH then with brine. The organic layer was concentrated in vacuo to give 27c as a pale pink solid (850 mg, 42%).

Synthesis of N-(2-(4-(4-fluorobenzylcarbamoyl)-5-hydroxy-1-(methyl-d₃)-6-oxo-1,6-dihydropyrimidin-2-yl)-(1,3-d₆-propan)-2-yl)-5-methyl-1,3,4-oxadiazole-2-carboxamide (108). To a stirring slurry of 19b (0.42 g, 2.55 mmol) in acetonitrile (3.7 mL) was added a drop of DMF. The mixture was cooled to 0° C., oxalyl chloride (0.2 mL, 2.43 mmol) was added over 20 min and the resulting reaction mixture was stirred at 0° C. for 2 h. In a separate round bottom flask, a solution of 27c (0.40 g, 1.16 mmol) in THF (11 mL) was cooled to 0° C., NMM (0.3 mL, 2.79 mmol) was added and the resulting slurry was stirred for 10 min. To this slurry, the previously prepared acid chloride solution was added over 20 min while maintaining the reaction at 0° C. The mixture was then stirred at 0° C. for 2 h. The resulting yellow slurry was concentrated in vacuo, the residue dissolved in CH₂Cl₂, and the resulting organic solution was washed with water (3 times) followed by brine, dried over Na₂SO₄, filtered and concentrated in vacuo. The crude product was purified by combi-flash chromatography using MeOH/CH₂Cl₂ to Compound 108 as an off-white solid (120 mg, 23%). ¹H NMR (400 MHz, DMSO-d₆): δ 12.22 (IH, s), 9.87 (1H, s), 9.10 (1H, s), 7.38 (2H, dd, J=6, 8 Hz), 7.16 (2H, t, J=9 Hz), 4.49 (2H, d, J=6 Hz), 2.55 (3H, s). MS (M+H): 454.2. HPLC (method: Luna C18 column-gradient method 5-100% ACN+0.1% TFA in 17.0 min with 3.0 min hold at 100% ACN, a 2 min hold at 70% ACN and a 3 min hold at 5% ACN; Wavelength: 254 nm): retention time: 14.65 min; 94.2% purity.

Example 7

Synthesis of N-(2-(4-(4-fluoro(benzyl-d₆)carbamoyl)-5-hydroxy-1-(methyl-d₃)-6-oxo-1,6-dihydropyrimidin-2-yl)-(1,3-d₆-propan)-2-yl)-5-methyl-1,3,4-oxadiazole-2-carboxamide (127)

Compound 127

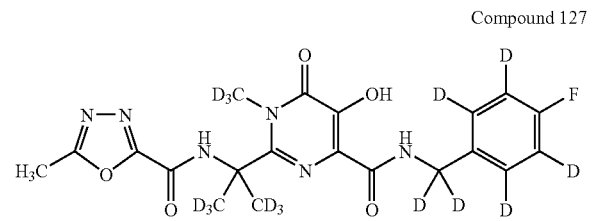

Compound 127 was prepared as outlined in Scheme 6 above utilizing 19b in place of 19c. Details of the synthesis are set forth below.

Synthesis of N-(2-(4-(4-fluoro(benzyl-d₆)carbamoyl)-5-hydroxy-1-(methyl-d₃)-6-oxo-1,6-dihydropyrimidin-2-yl)-(1,3-d₆-propan)-2-yl)-5-methyl-1,3,4-oxadiazole-2-carboxamide (127). To a solution of oxadiazole 19b (0.30 g, 1.82 mmol) and amine 27a (0.40 g, 1.14 mmol) stirring in DMF (13 mL) at 0° C., was added HATU (0.73 g, 1.94 mmol). The reaction mixture was stirred at 0° C. for 3 h, water was added and the solution was extracted repeatedly with CH₂Cl₂. The combined organic layers were washed with brine, dried over Na₂SO₄, filtered and concentrated in vacuo. Residual DMF was removed by overnight lyophilization. The crude product was purified by combi-flash chromatography using MeOH/CH₂Cl₂ to give Compound 127 as an off-white solid (130 mg, 25%). ¹H NMR (400 MHz, DMSO-d₆): δ 12.22 (IH, s), 9.87 (1H, s), 9.10 (1H, s), 2.61 (3H, s). MS (M+H): 460.2. HPLC (method: Luna C18 column-gradient method 5-100% ACN+0.1% TFA in 17.0 min with 3.0 min hold at 100% ACN, a 2 min hold at 70% ACN and a 3 min hold at 5% ACN; Wavelength: 254 nm): retention time: 14.65 min; 95.2% purity.

Evaluation of Metabolic Stability

Certain in vitro liver metabolism studies have been described previously in the following references, each of which is incorporated herein in their entirety: Obach, R S, Drug Metab Disp, 1999, 27:1350; Houston, J B et al., Drug Metab Rev, 1997, 29:891; Houston, J B, Biochem Pharmacol, 1994, 47:1469; Iwatsubo, T et al., Pharmacol Ther, 1997, 73:147; and Lave, T, et al., Pharm Res, 1997, 14:152.

Microsomal Assay: The metabolic stability of compounds of Formula I is tested using pooled liver microsomal incubations. Full scan LC-MS analysis is then performed to detect major metabolites. Samples of the test compounds, exposed to pooled human liver microsomes, are analyzed using HPLC-MS (or MS/MS) detection. For determining metabolic stability, multiple reaction monitoring (MRM) is used to measure the disappearance of the test compounds. For metabolite detection, Q1 full scans are used as survey scans to detect the major metabolites.

Experimental Procedures: Human liver microsomes are obtained from a commercial source (e.g., Absorption Systems L.P. (Exton, Pa.)). The incubation mixtures are prepared as follows:

| Reaction Mixture Composition | |
|---|---|
| Liver Microsomes | 1.0 mg/mL |
| NADPH | 1 mM |
| Potassium Phosphate, pH 7.4 | 100 mM |
| Magnesium Chloride | 10 mM |
| Test Compound | 1 µM. |

Incubation of Test Compounds with Liver Microsomes: The reaction mixture, minus cofactors, is prepared. An aliquot of the reaction mixture (without cofactors) is incubated in a shaking water bath at 37° C. for 3 minutes. Another aliquot of the reaction mixture is prepared as the negative control. The test compound is added into both the reaction mixture and the negative control at a final concentration of 1 µM. An aliquot of the reaction mixture is prepared as a blank control, by the addition of plain organic solvent (no test compound). The reaction is initiated by the addition of cofactors (not added to the negative controls), and then incubated in a shaking water bath at 37° C. Aliquots (200 µL) are withdrawn in triplicate at multiple time points (e.g., 0, 15, 30, 60, and 120 minutes) and combined with 800 µL of ice-cold 50/50 acetonitrile/dH₂O to terminate the reaction. The positive controls, testosterone and propranolol, as well as raltegravir, are each run simultaneously with the test compounds in separate reactions.

All samples are analyzed using LC-MS (or MS/MS). An LC-MRM-MS/MS method is used for metabolic stability. Also, Q1 full scan LC-MS methods are performed on the blank matrix and the test compound incubation samples. The Q1 scans serve as survey scans to identify any sample unique peaks that might represent the possible metabolites. The masses of these potential metabolites can be determined from the Q1 scans.

Without further description, it is believed that one of ordinary skill in the art can, using the preceding description and the illustrative examples, make and utilize the compounds of the present disclosure and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the disclosure. All the patents, journal articles and other documents discussed or cited above are herein incorporated by reference.

I claim:

1. A compound of Formula I:

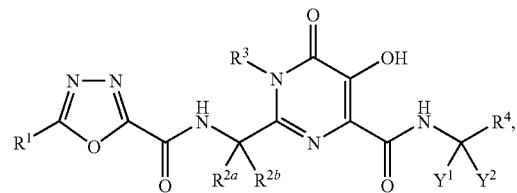

(I)

or a pharmaceutically acceptable salt, solvate, or hydrate thereof, wherein:
each of $R^1$, $R^{2a}$, $R^{2b}$, and $R^3$ is independently selected from $CH_3$, $CDH_2$, $CD_2H$, and $CD_3$;
$Y^1$ and $Y^2$ are each independently selected from H or D;
$R^4$ selected from:

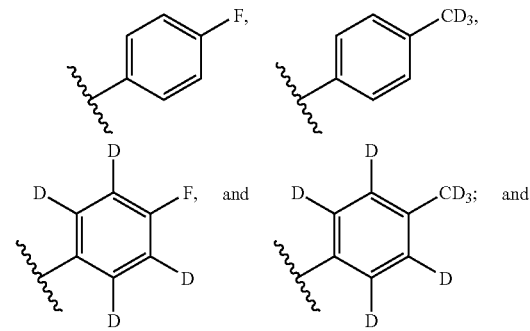

when each R is $CH_3$, at least one of $Y^1$ and $Y^2$ is D.

2. The compound of claim 1, wherein each of $R^1$, $R^{2a}$, $R^{2b}$ and $R^3$ is independently selected from $CH_3$, and $CD_3$.

3. The compound of claim 2, wherein $Y^1$ and $Y^2$ are the same.

4. The compound of claim 3, wherein $R^{2a}$ and $R^{2b}$ are the same and are selected from $CH_3$ and $CD_3$.

5. The compound of claim 4, wherein $R^4$ is selected from

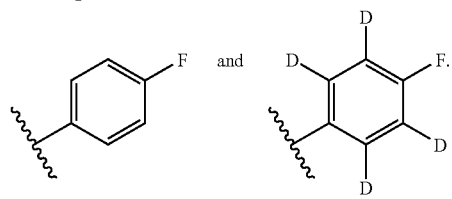

6. The compound of claim 5, wherein $R^4$ is

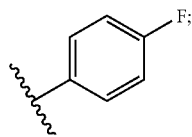

and the compound is selected from any one of the compounds set forth in the table below:

| Compound | $R^1$ | $R^{2a}$ | $R^{2b}$ | $R^3$ | $Y^1$ | $Y^2$ |
| --- | --- | --- | --- | --- | --- | --- |
| 101 | $CD_3$ | $CH_3$ | $CH_3$ | $CH_3$ | H | H |
| 102 | $CH_3$ | $CD_3$ | $CD_3$ | $CH_3$ | H | H |
| 103 | $CH_3$ | $CH_3$ | $CH_3$ | $CD_3$ | H | H |
| 104 | $CH_3$ | $CH_3$ | $CH_3$ | $CH_3$ | D | D |
| 105 | $CD_3$ | $CD_3$ | $CD_3$ | $CH_3$ | H | H |
| 106 | $CD_3$ | $CH_3$ | $CH_3$ | $CD_3$ | H | H |
| 107 | $CD_3$ | $CH_3$ | $CH_3$ | $CH_3$ | D | D |
| 108 | $CH_3$ | $CD_3$ | $CD_3$ | $CD_3$ | H | H |
| 109 | $CH_3$ | $CD_3$ | $CD_3$ | $CH_3$ | D | D |
| 110 | $CH_3$ | $CH_3$ | $CH_3$ | $CD_3$ | D | D |
| 111 | $CD_3$ | $CD_3$ | $CD_3$ | $CD_3$ | H | H |
| 112 | $CD_3$ | $CH_3$ | $CH_3$ | $CD_3$ | D | D |
| 113 | $CH_3$ | $CD_3$ | $CD_3$ | $CD_3$ | D | D |
| 114 | $CD_3$ | $CD_3$ | $CD_3$ | $CD_3$ | D | D. |

7. The compound of claim 5, wherein $R^4$ is

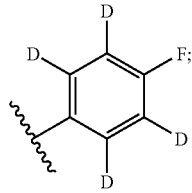

and the compound is selected from any one of the compounds set forth in the table below:

| Compound | $R^1$ | $R^{2a}$ | $R^{2b}$ | $R^3$ | $Y^1$ | $Y^2$ |
| --- | --- | --- | --- | --- | --- | --- |
| 115 | $CD_3$ | $CH_3$ | $CH_3$ | $CH_3$ | H | H |
| 116 | $CH_3$ | $CD_3$ | $CD_3$ | $CH_3$ | H | H |
| 117 | $CH_3$ | $CH_3$ | $CH_3$ | $CD_3$ | H | H |
| 118 | $CH_3$ | $CH_3$ | $CH_3$ | $CH_3$ | D | D |
| 119 | $CD_3$ | $CD_3$ | $CD_3$ | $CH_3$ | H | H |
| 120 | $CD_3$ | $CH_3$ | $CH_3$ | $CD_3$ | H | H |
| 121 | $CD_3$ | $CH_3$ | $CH_3$ | $CH_3$ | D | D |
| 122 | $CH_3$ | $CD_3$ | $CD_3$ | $CD_3$ | H | H |
| 123 | $CH_3$ | $CD_3$ | $CD_3$ | $CH_3$ | D | D |
| 124 | $CH_3$ | $CH_3$ | $CH_3$ | $CD_3$ | D | D |
| 125 | $CD_3$ | $CD_3$ | $CD_3$ | $CD_3$ | H | H |
| 126 | $CD_3$ | $CH_3$ | $CH_3$ | $CD_3$ | D | D |
| 127 | $CH_3$ | $CD_3$ | $CD_3$ | $CD_3$ | D | D |
| 128 | $CD_3$ | $CD_3$ | $CD_3$ | $CD_3$ | D | D. |

8. The compound of any one of claims 1 to 7, wherein any atom not designated as deuterium is present at its natural isotopic abundance.

9. A pyrogen-free pharmaceutical composition comprising a compound of any one of claims 1 to 7 and a pharmaceutically acceptable carrier.

* * * * *

UNITED STATES PATENT AND TRADEMARK OFFICE
CERTIFICATE OF CORRECTION

PATENT NO. : 7,687,509 B2  Page 1 of 1
APPLICATION NO. : 12/169367
DATED : March 30, 2010
INVENTOR(S) : Scott L. Harbeson It is certified that error appears in the above-identified patent and that said Letters Patent is hereby corrected as shown below:

Column 33, line 51 (Claim 2), please delete "$R^{2b}$" and insert --$R^{2b}$,-- therefor.

Signed and Sealed this

Fifteenth Day of June, 2010

David J. Kappos
*Director of the United States Patent and Trademark Office*